(12) United States Patent
Srivastava et al.

(10) Patent No.: US 9,357,916 B2
(45) Date of Patent: Jun. 7, 2016

(54) ANALYSIS AND VISUALIZATION OF OCT ANGIOGRAPHY DATA

(71) Applicant: Carl Zeiss Meditec, Inc., Dublin, CA (US)

(72) Inventors: Siddharth Srivastava, Antioch, CA (US); Utkarsh Sharma, San Leandro, CA (US); Mary K. Durbin, San Francisco, CA (US); Tilman Schmoll, Dublin, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 13/781,375

(22) Filed: Feb. 28, 2013

(65) Prior Publication Data

US 2013/0301008 A1 Nov. 14, 2013

Related U.S. Application Data

(63) Continuation of application No. 61/645,513, filed on May 10, 2012.

(60) Provisional application No. 61/691,219, filed on Aug. 20, 2012.

(51) Int. Cl.
*A61B 3/00* (2006.01)
*A61B 3/10* (2006.01)
(Continued)

(52) U.S. Cl.
CPC ............ *A61B 3/102* (2013.01); *G01B 9/02083* (2013.01); *G01B 9/02091* (2013.01);
(Continued)

(58) Field of Classification Search
CPC ........ A61B 3/14; A61B 3/102; A61B 3/0066; A61B 3/0073; A61B 3/1233; A61B 3/1241; G06T 7/0042; G06T 11/003; G06T 7/2006; G06T 2207/10101; G06T 2207/30041; G06T 19/00; G01B 9/02091; G01B 9/02083; G01N 2021/1787; G06F 19/321
USPC .......... 351/219, 221, 246; 382/131, 128, 130, 382/107, 132; 356/479
See application file for complete search history.

(56) References Cited

U.S. PATENT DOCUMENTS

| | | |
|---|---|---|
| 6,549,801 B1 | 4/2003 | Chen et al. |
| 7,301,644 B2 | 11/2007 | Knighton et al. |

(Continued)

FOREIGN PATENT DOCUMENTS

| | | |
|---|---|---|
| WO | 2010/030159 A2 | 3/2010 |
| WO | 2010/129494 A2 | 11/2010 |

(Continued)

OTHER PUBLICATIONS

Herfkens, Robert. "Computational Visualization of 4D Cardiac Flow". https://web.archive.org/web/20110810120411/http://www.nvidia.com/object/quadro-fermi-video-view04.html.*

(Continued)

*Primary Examiner* — Bumsuk Won
*Assistant Examiner* — Collin X Beatty
(74) *Attorney, Agent, or Firm* — Morrison & Foerster LLP (57) ABSTRACT

Methods for analyzing and visualizing OCT angiography data are presented. In one embodiment, an automated method for identifying the foveal avascular zone in a two dimensional en face image generated from motion contrast data is presented. Several 3D visualization techniques are presented including one in which a particular vessel is selected in a motion contrast image and all connected vessels are highlighted. A further embodiment includes a stereoscopic visualization method. In addition, a variety of metrics for characterizing OCT angiography image data are described.

13 Claims, 5 Drawing Sheets

(51) Int. Cl.
*G06K 9/00* (2006.01)
*G01B 9/02* (2006.01)
*G06T 19/00* (2011.01)
*G06T 7/20* (2006.01)

(52) U.S. Cl.
CPC .............. *G06T 7/2006* (2013.01); *G06T 19/00* (2013.01); *G06T 2207/10101* (2013.01); *G06T 2207/30041* (2013.01); *G06T 2210/41* (2013.01)

(56) References Cited

U.S. PATENT DOCUMENTS

| | | | |
|---|---|---|---|
| 7,359,062 | B2 | 4/2008 | Chen et al. |
| 8,079,711 | B2 | 12/2011 | Stetson et al. |
| 2003/0208326 | A1 | 11/2003 | Chen et al. |
| 2004/0076262 | A1* | 4/2004 | Shao et al. ............ 378/196 |
| 2005/0171438 | A1 | 8/2005 | Chen et al. |
| 2007/0019846 | A1 | 1/2007 | Bullitt et al. |
| 2008/0025570 | A1 | 1/2008 | Fingler et al. |
| 2008/0100612 | A1* | 5/2008 | Dastmalchi et al. ........ 345/418 |
| 2008/0159604 | A1 | 7/2008 | Wang et al. |
| 2008/0291463 | A1 | 11/2008 | Milner et al. |
| 2009/0005693 | A1 | 1/2009 | Brauner et al. |
| 2009/0268162 | A1* | 10/2009 | Stetson et al. ............ 351/246 |
| 2009/0270738 | A1* | 10/2009 | Izatt et al. ............ 600/476 |
| 2010/0027857 | A1* | 2/2010 | Wang ............ 382/128 |
| 2010/0113900 | A1* | 5/2010 | Shakespeare et al. ....... 600/316 |
| 2010/0159497 | A1 | 6/2010 | Kimia et al. |
| 2010/0189334 | A1* | 7/2010 | Tomidokoro et al. ........ 382/131 |
| 2010/0240986 | A1* | 9/2010 | Stiles ............ 600/424 |
| 2010/0245770 | A1* | 9/2010 | Zhang et al. ............ 351/219 |
| 2011/0034803 | A1 | 2/2011 | Stetson |
| 2011/0063573 | A1* | 3/2011 | Meyer et al. ............ 351/246 |
| 2011/0103657 | A1 | 5/2011 | Kang et al. |
| 2011/0109881 | A1* | 5/2011 | Munger et al. ............ 351/221 |
| 2011/0164791 | A1* | 7/2011 | Bajraszewski et al. ....... 382/107 |
| 2011/0169978 | A1* | 7/2011 | Lasser et al. ............ 348/222.1 |
| 2011/0243408 | A1* | 10/2011 | Takama ............ 382/128 |
| 2012/0035454 | A1* | 2/2012 | Tearney et al. ............ 600/407 |
| 2012/0053904 | A1* | 3/2012 | Yuasa et al. ............ 702/189 |
| 2012/0063665 | A1* | 3/2012 | Wang et al. ............ 382/134 |
| 2012/0075638 | A1* | 3/2012 | Rollins et al. ............ 356/479 |
| 2012/0120408 | A1* | 5/2012 | Yasuno et al. ............ 356/479 |
| 2012/0140171 | A1* | 6/2012 | Hirose et al. ............ 351/206 |
| 2012/0218516 | A1 | 8/2012 | Imamura |
| 2012/0274745 | A1* | 11/2012 | Russell ............ 348/46 |
| 2012/0277570 | A1 | 11/2012 | Todor et al. |
| 2013/0018254 | A1* | 1/2013 | Drucker ............ 600/424 |
| 2013/0094725 | A1* | 4/2013 | Gulsun et al. ............ 382/128 |
| 2013/0215235 | A1* | 8/2013 | Russell ............ 348/47 |
| 2014/0049632 | A1* | 2/2014 | Hemmer ............ 348/79 |
| 2014/0293222 | A1* | 10/2014 | Coelho et al. ............ 351/206 |

FOREIGN PATENT DOCUMENTS

| | | |
|---|---|---|
| WO | 2010/131944 A2 | 11/2010 |
| WO | 2010/138645 A2 | 12/2010 |
| WO | 2010/129494 A3 | 2/2011 |
| WO | 2011/097631 A2 | 8/2011 |
| WO | 2011/097631 A3 | 11/2011 |

OTHER PUBLICATIONS

Makita, S. and Yasuno, Y. "Optical coherence angiography for the eye". SPIE, 2009, 10.1117/2.1200905.1578.*
Dae Yu Kim, Jeff Fingler, Robert J. Zawadzki, Susanna S. Park, Lawrence S. Morse, Daniel M. Schwartz, Scott E. Fraser, and John S. Werner. Noninvasive Imaging of the Foveal Avascular Zone with High-Speed, Phase-Variance Optical Coherence Tomography. Investigative Ophthalmology & Visual Science, Jan. 2012, vol. 53, No. 1.*
Delia Cabrera DeBuc (2011). A Review of Algorithms for Segmentation of Retinal Image Data Using Optical Coherence Tomography, Image Segmentation, Dr. Pei-Gee Ho (Ed.), ISBN: 978-953-307-228-9, InTech, Available from: http://www.intechopen.com/books/image-segmentation/a-review-of-algorithms-forsegmentation-of-retinal-image-data-using-optical-cohere.*
Andrew Rollins, Siavash Yazdanfar, Jennifer Barton, Joseph A. Izatt. Real-time in vivo color Doppler optical coherence tomography. Journal of Biomedical Optics 7(1), 123-129 (Jan. 2002).*
Charles Riva, Benjamin Ross, and George B. Benedek. Laser Doppler measurements of blood flow in capillary tubes and retinal arteries. Investigative Ophthalmology Nov. 1972.*
Kevin "Chaim" Herman. Crossing the Challenging Aortic Bifurcation. Endovascular Today I Jan. 2012.*
Al-Diri et al., "Automated Analysis of Retinal Vascular Network Connectivity", Computerized Medical Imaging and Graphics, vol. 34, 2010, pp. 462-470.
An et al., "Optical Microangiography provides Correlation between Microstructure and Microvasculature of Optic Nerve Head in Human Subjects", Journal of Biomedical Optics, vol. 17, No. 11, Nov. 2012, pp. 116018-1-116018-6.
Avakian et al., "Fractal Analysis of Region-Based Vascular Change in the Normal and Non-Proliferative Diabetic Retina", Current Eye Research, vol. 24, No. 4, 2002, pp. 274-280.
Fingler et al., "Mobility and Transverse Flow Visualization using Phase Variance Contrast with Spectral Domain Optical Coherence Tomography", Optics Express, vol. 15, No. 20, Oct. 1, 2007, pp. 12636-12653.
Fingler et al., "Volumetric Microvascular Imaging of Human Retina using Optical Coherence Tomography with a Novel Motion Contrast Technique", Optics Express, vol. 17, No. 24, Nov. 23, 2009, pp. 22190-22200.
Ganesan et al., "Development of an Image-Based Network Model of Retinal Vasculature", Annals of Biomedical Engineering, vol. 38, No. 4, Apr. 2010, pp. 1566-1585.
Jia et al., "Quantitative OCT Angiography of Optic Nerve Head Blood Flow", Biomedical Optics Express, vol. 3, No. 12, Dec. 1, 2012, pp. 3127-3137.
John et al., "Dimensions of the Foveal Avascular Zone using the Heidelberg Retinal Angiogram-2 in Normal Eyes", Indian Journal of Ophthalmol, vol. 59, No. 1, 2011, 6 pages.
Kim et al., "In vivo Volumetric Imaging of Human Retinal Circulation with Phase-Variance Optical Coherence Tomography", Biomedical Optics Express, vol. 2, No. 6, Jun. 1, 2011, pp. 1504-1513.
Kim et al., "Noninvasive Imaging of the Foveal Avascular Zone with High-Speed, Phase-Variance Optical Coherence Tomography", Investigative Ophthalmology & Visual Science, vol. 53, No. 1, Jan. 2012, pp. 85-92.
Leitgeb et al., "Real-Time Assessment of Retinal Blood Flow with Ultrafast Acquisition by Color Doppler Fourier Domian Optical Coherence Tomography", Optics Express, vol. 11, No. 23, Nov. 17, 2003, pp. 3116-3121.
Leitgeb et al., "Ultrahigh Resolution Fourier Domain Optical Coherence Tomography", Optics Express, vol. 12, No. 10, May 17, 2004, pp. 2156-2165.
Liu et al., "Intensity-Based Modified Doppler Variance Algorithm: Application to Phase Instable and Phase Stable Optical Coherence Tomography Systems", Optics Express, vol. 19, No. 12, Jun. 6, 2011, pp. 11429-11440.
Makita et al., "Comprehensive in vivo Micro-Vascular Imaging of the Human Eye by Dual-Beam-Scan Doppler Optical Coherence Angiography", Optics Express, vol. 19, No. 2, Jan. 17, 2011, pp. 1271-1283.
Makita et al., "Optical Coherence Angiography", Optics Express, vol. 14, No. 17, Aug. 21, 2006, pp. 7821-7840.
Mariampillai et al., "Optimized Speckle Variance OCT Imaging of Microvasculature", Optics Letters, vol. 35, No. 8, Apr. 15, 2010, pp. 1257-1259.
Popovic et al., "Noninvasive Imaging of Human Foveal Capillary Network Using Dual-Conjugate Adaptive Optics", Investigative Ophthalmology & Visual Science, vol. 52, No. 5, Apr. 2011, pp. 2649-2655.

(56) References Cited

OTHER PUBLICATIONS

Ramezani et al., "Agreement Between Clinical Estimation and a New Quantitative Analysis by Photoshop Software in Fundus and Angiographic Image Variables", Int. Ophthalmol, vol. 29, 2009, pp. 439-449.

Schmoll et al., "Imaging of the Parafoveal Capillary Network and its Integrity Analysis using Fractal Dimension", Biomedical Optics Express, vol. 2, No. 5, May 1, 2011, pp. 1159-1168.

Spaide et al., "Fundus Autofluorescence and Central Serous Chorioretinopathy", American Academy of Ophthalmology, vol. 112, No. 5, May 2005, pp. 825-833.

Wang et al., "Depth-Resolved Imaging of capillary Networks in Retina and Choroid using Ultrahigh Sensitive Optical Microangiography", Optics Letters, vol. 35, No. 9, May 1, 2010, pp. 1467-1469.

Wang et al., "Frequency Domain Phase-Resolved Optical Doppler and Doppler Variance Tomography", Optics Communications, vol. 242, 2004, pp. 345-350.

Wang et al., "Imaging Retinal Capillaries Using Ultrahigh-Resolution Optical Coherence Tomography and Adaptive Optics", Investigative Ophthalmology & Visual Science, vol. 52, No. 9, Aug. 2011, pp. 6292-6299.

Wang et al., "Three Dimensional Optical Angiography", Optics Express, vol. 15, No. 7, Apr. 2, 2007, pp. 4083-4097.

White et al., "In vivo Dynamic Human Retinal Blood Flow Imaging using Ultra-High-Speed Spectral Domain Optical Doppler Tomography", Optics Express, vol. 11, No. 25, Dec. 15, 2003, pp. 3490-3497.

Yazdanfar et al., "Imaging and Velocimetry of the Human Retinal Circulation with Color Doppler Optical Coherence Tomography", Optics Letters,, vol. 25, No. 19, Oct. 1, 2000, pp. 1448-1450.

Zhao et al., "Doppler Standard Deviation Imaging for Clinical Monitoring of in vivo Human Skin Blood Flow", Optics Letters, vol. 25, No. 18, Sep. 15, 2000, pp. 1358-1360.

Zheng et al., "Automated Segmentation of Foveal Avascular Zone in Fundus Fluorescein Angiography", Investigative Ophthalmology & Visual Science, vol. 51, No. 7, Jul. 2010, pp. 3653-3659.

International Search Report and Written Opinion received for PCT Patent Application No. PCT/EP2013/059560, mailed on Aug. 27, 2013, 6 pages.

Non Final Office Action received for U.S. Appl. No. 13/543,373, mailed on Sep. 25, 2012, 9 pages.

Notice of Allowance received for U.S. Appl. No. 13/543,373, mailed on Jan. 2, 2013, 5 pages.

An et al., "In Vivo Volumetric Imaging of Vascular Perfusion within Human Retina and Choroids with Optical Micro-Angiography", Optics Express, vol. 16, No. 15, 2008, pp. 11438-11452.

An et al., "Ultrahigh Sensitive Optical Microangiography for in Vivo Imaging of Microcirculations within Human Skin Tissue Beds", Optics Express, vol. 18, No. 8, 2010, pp. 8220-8228.

Kirkpatrick et al., "OCT-Based Elastography for Large and Small Deformations", Optics Express, vol. 14, No. 24, Nov. 27, 2006, pp. 11585-11597.

Schmitt, Joseph M., "OCT Elastography: Imaging Microscopic Deformation and Strain of Tissue", Optics Express, vol. 3, No. 6, Sep. 14, 1998, pp. 199-211.

Zotter et al., "Visualization of Microvasculature by Dual-Beam Phase-Resolved Doppler Optical Coherence Tomography", Optics Express, vol. 19, No. 2, 2011, pp. 1217-1227.

\* cited by examiner

ANALYSIS AND VISUALIZATION OF OCT ANGIOGRAPHY DATA

PRIORITY

The following application claims priority to U.S. Provisional Application Ser. No. 61/645,513 filed May 10, 2012 and U.S. Provisional Application Ser. No. 61/691,219 filed Aug. 20, 2012, the contents of both of which are hereby incorporated by reference.

TECHNICAL FIELD

The present invention relates to medical imaging, and in particular to analysis and visualization methods for data acquired through optical coherence tomography.

BACKGROUND

Optical coherence tomography is a noninvasive, noncontact imaging modality that uses coherence gating to obtain high-resolution cross-sectional images of tissue microstructure. In Fourier domain OCT (FD-OCT), the interferometric signal between light from a reference and the back-scattered light from a sample point is recorded in the frequency domain rather than the time domain. After a wavelength calibration, a one-dimensional Fourier transform is taken to obtain an A-line spatial distribution of the object scattering potential. The spectral information discrimination in FD-OCT can be accomplished by using a dispersive spectrometer in the detection arm in the case of spectral-domain OCT (SD-OCT) or rapidly tuning a swept laser source in the case of swept-source OCT (SS-OCT).

Recently there has been a lot of interest in using intensity based and phase-sensitive based OCT techniques, collectively named OCT Angiography, to map the retinal vasculature or identify regions with flow in the tissue (see for example An et al. "Optical microangiography provides correlation between microstructure and microvasculature of optic nerve head in human subjects," J. Biomed. Opt. 17, 116018 (2012), Zhao et al., "Doppler standard deviation imaging for clinical monitoring of in vivo human skin blood flow," Optics Letters 25, 1358-1360 (2000), Fingler et al. "Mobility and transverse flow visualization using phase variance contrast with spectral domain optical coherence tomography" Optics Express. Vol. 15, No. 20. pp 12637-12653 (2007), Makita et al., "Optical Coherence Angiography," Optics Express, 14(17), 7821-7840 (2006), Mariampillai et al., "Optimized speckle variance OCT imaging of microvasculature," Optics Letters 35, 1257-1259 (2010), and Wang et al., "Frequency domain phase-resolved optical Doppler and Doppler variance tomography" Optics Communications 242 345-350 (2004) hereby incorporated by reference). OCT Angiography provides a non-invasive technique to visualize and indirectly quantify the integrity of retinal circulation pathways. Anomalies in retinal circulation have a direct relation to ocular pathologies, especially within the macula, wherein compromised hemo-dynamics may not only be related to decreased visual acuity, but could also be a surrogate biomarker for ocular pathologies like retinal vein occlusion (RVO), diabetic retinopathy (DR), and intra retinal microvasculature abnormality (IRMA). Specifically, correlation between retinal vasculature and blood flow are attributes of interest in a number of ocular defects. DR and RVO pathologies that could lead to early changes to the vascular structure and function, and may, in turn, be etiologic to numerous complications like macular edema, retinal ischemia and optic neuropathy. For these cases, quantification and visualization of vasculature, capillaries and flow can be a versatile diagnostic tool. For example, ischemic regions in the retina can be mapped to evaluate the extent of damage and further management of the disease. In addition to the vascular rich retina, there is a small area in the macula, at the fovea, which is devoid of any capillaries. This is called the Foveal Avascular zone (FAZ), and abnormal changes in the size of this region are also indicative of pathologies like ischemic maculopathy and DR. The quantification of the FAZ and measuring changes in its size over time can be a clinically significant numerical score for disease presence and progression, especially for DR.

Conventional techniques to visualize retinal vasculature are invasive in nature, and use pharmacological techniques to modify contrast in the imaged retina. Contemporary clinical practice involves injection of a fluorescent dye (such as fluorescein or indocyanine green (ICG)) into the systemic circulation, and the eye is then scanned to generate an image, which selectively shows the path of the dye through the vascular network (FA, Fluorescein Angiography). No information of the depth structure of the vasculature is captured by this method. In contrast, vascular images generated by examining the OCT intensity or phase signal are non-invasive, and provide comparable fidelity in capturing the existing vascular network with blood flow contrast along with its depth encoding.

There have been a few descriptions detailing the detection of FAZ in contemporary literature, but all the methods discussed are either manual, performed by experts, or are semi-automated, requiring an informed bootstrapping of the downstream method with a manually selected starting point or region. A few relevant publications, and references therein, serve to inform about the existing prior art (see for example Kim et al. "Noninvasive Imaging of the Foveal Avascular Zone with High-Speed, Phase-Variance Optical Coherence Tomography" Investigative Ophthalmology & Visual Science, 53 (1), 85-92 (2012), Zheng et al. "Automated segmentation of foveal avascular zone in fundus fluorescein angiography" Retina. 51(7): 3653-3659 (2010), Yong et al. "Novel Noninvasive Detection of the Fovea Avascular Zone Using Confocal Red-Free Imaging in Diabetic Retinopathy and Retinal Vein Occlusion" Retina. 52: 2649-2655 (2011), and Wang et al. "Imaging Retinal Capillaries Using Ultrahigh-Resolution Optical Coherence Tomography and Adaptive Optics" Invest. Ophthalmol. Vis. Sci. 52. 6292-6299 (2011) hereby incorporated by reference).

Diagnostically, changes to both the vascular and the typically avascular retina are important indicators of developing retinal pathologies. Although visualization of the vascular structure helps in boosting the diagnostic efficacy of this imaging technique, it can be further leveraged by augmenting the visualization with some salient quantifications and metrics derived from the identified vascular and avascular sections of the retina. The primary quantity of interest is the global or structure-specific retinal blood flow kinetics, which can be challenging to quantify because of low flow velocities relative to the temporal resolution of the technique, and the almost perpendicular orientation of the capillaries with respect to the probing beam. In addition to visualization, derived quantifiers from the angiography data which serve to aid in differentiating capillary networks in healthy and diseased eyes are also desirable.

Recently, a few research groups have explored quantitative methods for angiography data to construct meaningful numerical indicators of vascular pathology. Techniques such as fractal dimension analysis have been used to study vessel morphology, distribution and allied features. Avakian et al. demonstrated the use of fractal characterization of fluorescein angiography (FA) images of the human retina to distinguish between healthy and diseased retina (see for example Avakian, et al., "Fractal analysis of region-based vascular change in the normal and non-proliferative diabetic retina," Curr. Eye Res. 24, 274-280, 2002). Schmoll et al. applied a related fractal dimension algorithm to analyze the integrity of the parafoveal capillary network non-invasively using OCT angiography images (see for example Schmoll et al. "Imaging of the parafoveal capillary network and its integrity analysis using fractal dimension" Biomed. Opt. Express 2, 1159-1168, 2011). Also, Jia et al. and An et al. applied simpler vessel density measurements to quantitatively evaluate the capillary network within the human optic nerve head using OCT angiography methods (see for example Jia et al., "Quantitative OCT angiography of optic nerve head blood flow," Biomed. Opt. Express 3, 3127-3137, 2012 and An et al., "Optical microangiography provides correlation between microstructure and microvasculature of optic nerve head in human subjects," J. Biomed. Opt. 17, 116018, 2012).

One piece of important anatomical information that is captured by OCT angiography is the depth information, or the spatial distribution of the vessels in the retinal tissue. To visualize the complex capillary networks and to make use of the additional depth information gained by OCT angiography compared to traditional angiography methods such as FA, OCT angiography data is often displayed as 2D projections with the color encoded depth information (see Kim et al. "In vivo volumetric imaging of human retinal circulation with phase variance OCT," Biomedical Optics Express, 2(6), 1504-1513 (2011)). Such 2D projections at least allow distinguishing capillary layers of different depths. They however lack the 3D impression and also don't provide easily accessible information of which larger retinal vessels feed and drain different capillary network regions.

Retinal vessel connectivity measures are also known for fundus photography, they however only focus on a few major retinal vessels in 2D fundus images, rather than visualizing the supply of dense, complex parafoveal capillary networks (see for example Al-Diri et al. "Automated analysis of retinal vascular network connectivity," Computerized Medical Imaging and Graphics, 34, 462-470 (2010)). Ganesan et al. investigates the connectivity of vessels in mouse retinas from the largest vessels to the smallest capillaries in confocal microscopy images in order to develop a network model (see for example Ganesan et al. "Development of an Image-Based Network Model of Retinal Vasculature," Annals of Biomedical Engineering 38(4) 1566-1585 (2010)). They however don't describe using this as a way to interactively visualize human angiography acquisitions.

SUMMARY

The method described herein is a non-invasive, computational technique to generate images of retinal vasculature (or blood flow) that are then used to either extract various diagnostically relevant metrics related to retinal micro-circulation, and/or can subsequently be used to visualize the vascular and capillary structure in relation to the structure of the retinal tissue. The anatomical location of the vasculature is defined as locations where there is an appreciable motion contrast, which is typically due to flow of blood. There are a variety of OCT based methods to detect motion contrast such as Doppler OCT, speckle or intensity variance, and phase-resolved methods. In most of these methods, the motion contrast is determined by obtaining at least two OCT measurements at approximately the same location, where the two measurements are separated in time by a pre-determined interval and by applying an algorithm to look at the changes in the complex OCT signal or its components such as intensity or phase. The accuracy of these measurements can be improved by minimizing motion related errors including but not limited to removing signal due to bulk motion of the sample in the axial direction.

In a preferred embodiment of the present invention, the vascular structure extracted is post-processed to remove outliers and smooth the vessel structure. This derived structure is then depth coded and displayed over the rendered retinal anatomy (magnitude image). Further, the post-processed vascular structure within a specific depth range can be summed or integrated along the axial direction to generate a projection map that shows the vasculature as an en face view, devoid of any depth information. By examining the order or intensity statistics of this image, the regions devoid of any vasculature (such as the FAZ) can be delineated automatically, and its shape and size can be quantified. Alternatively, previously acquired fundus images, along with a fovea detector, can be registered to this synthetic en face image of the vasculature to assist in the detection of the fovea around which there is a high chance of finding the FAZ. The proposed invention deviates from the known prior art by detailing a completely automated (no manual intervention) method to accurately determine the capillary devoid regions of retina, by examination of the statistical properties of the intensity content of the retinal image which preferentially contrasts vascular regions.

In addition to the avascular zone, other metrics, like the vasculature density, capillary density, vessel geometry, capillary diameter, inter-capillary distance, area bounded by capillary loops, etc. can be determined by standard mathematical models and tools. These metrics can be identified in the vicinity of the fovea, or in other areas of interest, such as the perifoveal or peripapillary regions, the papillomacular bundle, or within the optic nerve head. This technique could be further extended to automatically identify regions of retinal ischemia in pathologies such as BRVO and CRVO. Furthermore, these techniques could also assist in identifying intraretinal microvascular abnormalities (IRMA). IRMA is typically a DR-related condition that results in areas of capillary dilatation and intraretinal formation of new capillary beds. Often the IRMA related new vessel formation occurs in retinal tissues to act as shunts through areas of nonperfusion or ischemia. Change in the metrics defined above could be used as a criterion to monitor if there has been new growth of vasculature or change in the regions of non-perfusion or ischemia.

In a further embodiment of the invention, a novel method for effectively visualizing OCT angiography acquisitions in a meaningful way and quantitatively characterizing vasculature networks is presented. The examiner could select a vessel within an OCT angiography acquisition and the program would show all connecting vessels down to the capillary network. The information about the connectivity of different retinal vessels may also be used to quantitatively evaluate OCT angiography acquisitions and compare them to a normative database.

DETAILED DESCRIPTION

Figure 1:
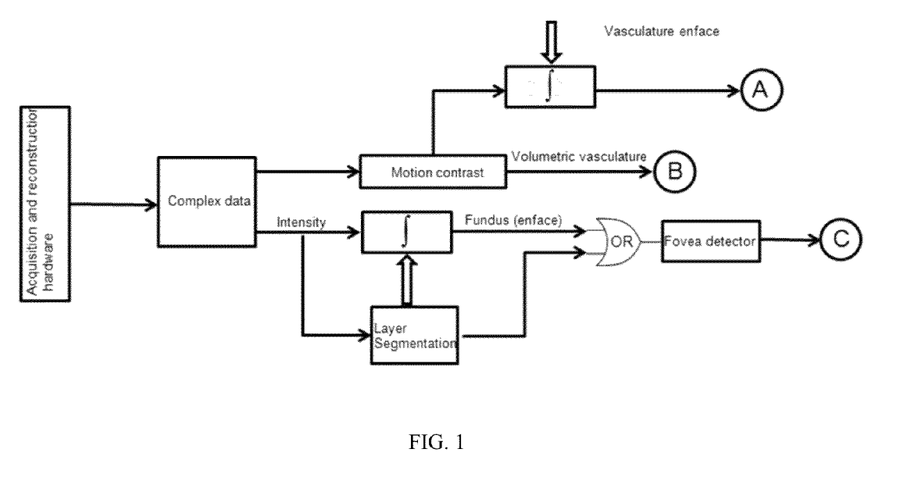
FIG. 1 shows a flow chart of various step involved with processing motion contrast OCT data according to the present invention.

Preferred and alternative embodiments for the processing of vasculature enhanced OCT data are illustrated in the schematic of FIG. 1, and its various components will be discussed in detail below.

Figure 2:
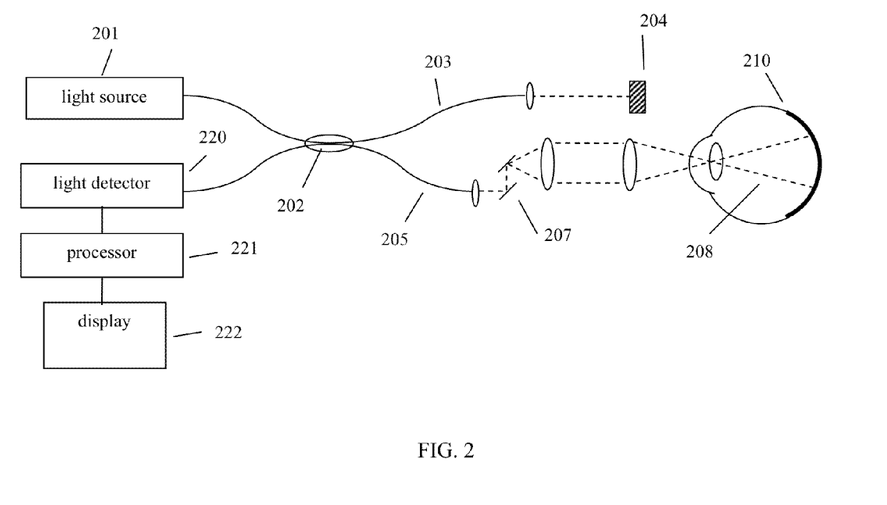
FIG. 2 illustrates a generalized ophthalmic OCT imaging system that could be used for collection of motion contrast data.

OCT data can be collected with any type of OCT system employing a variety of scan patterns, for example, a spectral domain OCT system, or a swept source OCT system, employing laser sources of different wavelength like 840 nm or 1060 nm. A diagram of a generalized OCT system is shown in FIG. 2. Light from source 201 is routed, typically by optical fiber 205, to illuminate the sample 210, a typical sample being tissues in the human eye. The source 201 can be either a broadband light source with short temporal coherence length in the case of SD-OCT or a wavelength tunable laser source in the case of SS-OCT. The light is scanned, typically with a scanner 207 between the output of the fiber and the sample, so that the beam of light (dashed line 208) is scanned laterally (in x and y) over the area or volume to be imaged. Light scattered from the sample is collected, typically into the same fiber 205 used to route the light for sample illumination. Reference light derived from the same source 201 travels a separate path, in this case involving fiber 203 and retro-reflector 204 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 202, to form light interference in a detector 220. Although a single fiber port is shown going to the detector, those skilled in the art recognize that various designs of interferometers can be used for balanced or unbalanced detection of the interference signal. The output from the detector is supplied to a processor 221. The results can be stored in the processor 221 or displayed on display 222. The processing and storing functions may be localized within the OCT instrument or functions may be performed on an external processing unit to which the collected data is transferred. This unit could be dedicated to data processing or perform other tasks which are quite general and not dedicated to the OCT device.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system capable of generating data for functional analysis.

The interference causes the intensity of the interfered light to vary across the spectrum. The Fourier transform of the interference light reveals the profile of scattering intensities at different path lengths, and therefore scattering as a function of depth (z-direction) in the sample (see for example Leitgeb et al. "Ultrahigh resolution Fourier domain optical coherence tomography," Optics Express 12(10):2156 (2004)). Typically, the Fourier transform results in complex data, and the absolute values of the complex data are tabulated to construct the intensity image. The complex OCT signal also encodes information related to the phase shifts arising from local sample motion, and can be used to deduce quantities related to physical motion of dominant scatterers in the sample with high sensitivity. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected.

Ideally the data will be collected while monitoring and correcting for any motion as described in US Patent Publication No. 2012/0249956 hereby incorporated by reference. Any one of a number of OCT angiography techniques (phase variance, speckle variance, Doppler, ultrahigh sensitive optical microangiography (UHS-OMAG), etc.) can be applied to the resulting complex OCT data set to examine the motion contrast. The result of this analysis can provide an image containing the volumetric definition of the location of the blood vessels as hyperintense signals (see for example Kim et al. "In vivo volumetric imaging of human retinal circulation with phase variance OCT," Biomedical Optics Express, 2(6), 1504-1513 (2011)). Intensity based local searches or global approaches can be used on the magnitude images to extract prominent layers which are then used as boundaries for the summation of intensities. The boundaries extracted serve to include only that tissue extent in the summation which is known a-priori to have blood vessels. The result of this summing procedure is a flat view (projection) of the volume looking along (and into) the imaging axis, and the features in this projection (en face vasculature image) capture the vascular distribution (Process A in FIG. 1). Since the summation integrates out the depth along the axial direction, this view only captures the omnibus morphology of the vasculature, and not position in the depth direction.

Figure 3:
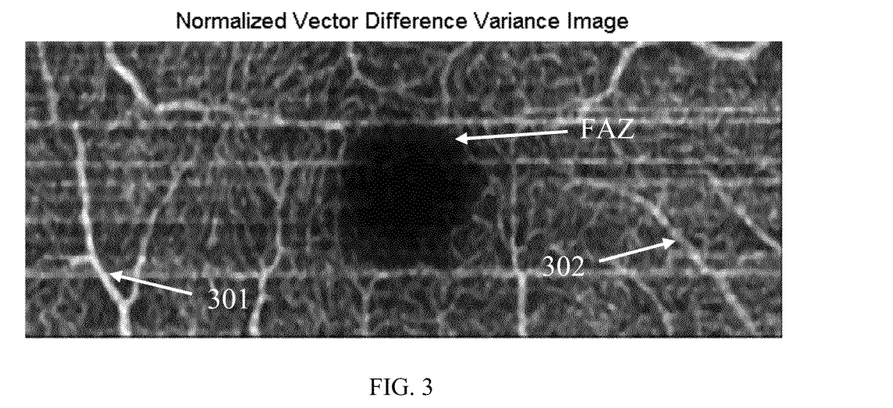
FIG. 3 shows an en face vasculature image generated from OCT data using normalized vector difference variance.

FIG. 3 shows the en face vasculature image generated by selective summation (FIG. 1, Process A) through the motion contrasted volume generated by performing normalized vector difference variance as described in US Patent Publication No. 2012/0277579, hereby incorporated by reference. The bright vasculature indicated by the arrows 301 and 302 stands out against the dark background. The absence of vessels in the central region indicates the foveal avascular zone (FAZ). It is clear from FIG. 3 that the technique generates a good representation of the blood circulatory circuit of the retina. In this example, the bounding layers used for the selective summation were the inner limiting membrane (ILM) and a layer positioned 50 microns below it. Anatomically the vasculature is distributed in the 3 major sections of the retina (FIG. 4): the superficial capillary plexus (SCP), intermediate capillary plexus (ICP) and the deep capillary plexus (DCP) (see for example Kim et al. "Noninvasive Imaging of the Foveal Avascular Zone with High-Speed, Phase-Variance Optical Coherence Tomography" Investigative Ophthalmology & Visual Science, 53 (1), 85-92 (2012) hereby incorporated by reference). Each of these plexus is made up of a finite number of retinal layers, which, in an alternate embodiment, can be used as bounding layers for selective summation to generate vasculature en face views showing the three specific types of vasculature networks. Selective summation is not required to generate an en face image and other examples of selective summations or other ways to represent a plurality of intensity values as a single representative value (e.g. integration, summing, minimum, maximum, median value, etc.) can be envisioned by those skilled in the art (see for example U.S. Pat. No. 7,301,644, US Patent Publication No. 2011/0034803 and US Patent Publication No. 2008/0100612 hereby incorporated by reference).

Figure 4:
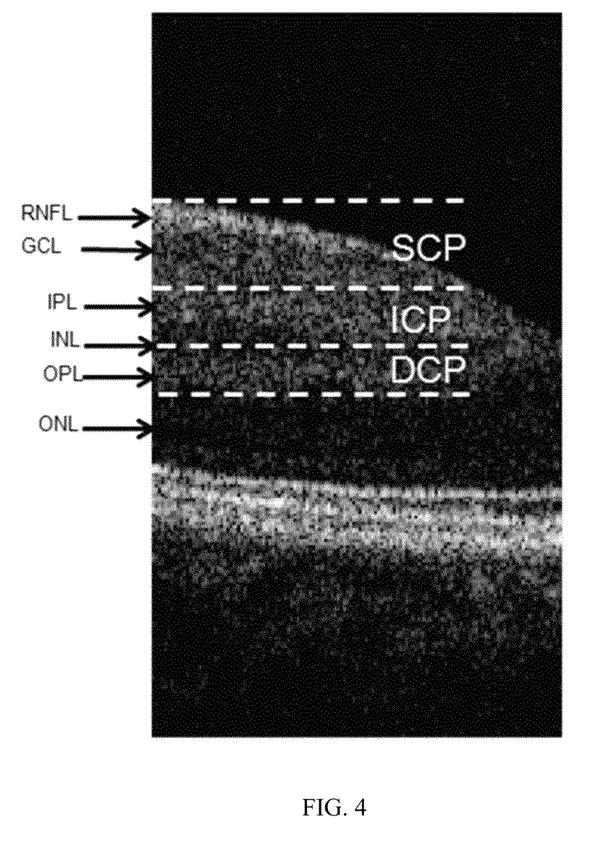
FIG. 4 shows an OCT image of the retina illustrating three different plexus and the layers that they include.
Figure 5:
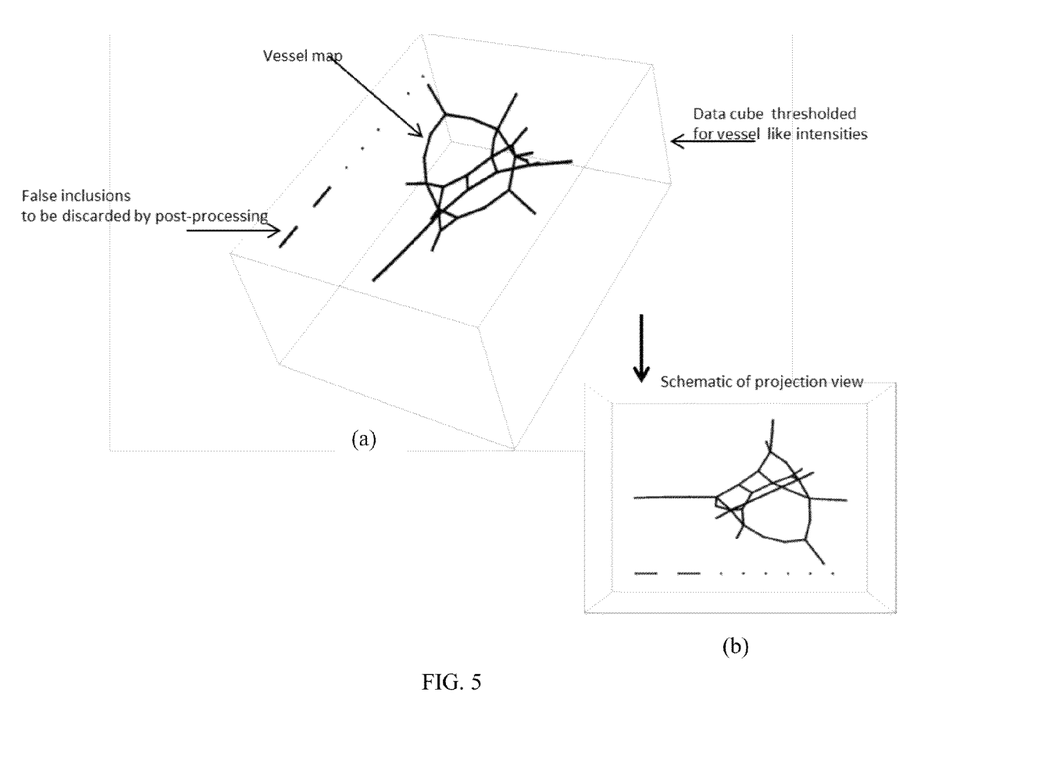
FIG. 5a shows a 3D visualization of OCT angiography data and FIG. 5b shows a corresponding 2D projection image.

As mentioned previously, the projection views are devoid of any depth information, because the hyperintense pixels, which signal the presence of vasculature are summed along the axial direction. Anatomically, the retinal vasculature is distributed in the 3-dimensional space of the retinal tissue, with the distribution and characteristics of the vasculature varying also within each specific plexus (FIG. 4). In one preferred embodiment of the present invention, the depth information in the view presented in FIG. 3 can be preserved by explicitly using the volumetric definition of the vasculature (after motion contrasting the phase data), and rendering the volume in three-dimensions (3D, process B in FIG. 1). Typically, this process, which extends process B, would entail preserving the high intensity locations in the acquired volume using a thresholding or selection criteria, and performing some post-processing to enforce the anatomical connectivity of the vasculature. A schematic of the expected form of the 3D vasculature map is shown in FIG. 5a, where the black lines trace out the vessel path in 3D space. The corresponding 2D projection view is illustrated in FIG. 5b. The 3D visualization mode will provide a visual representation of the vascular architecture/distribution in the space of the imaged retina. The data included in the 3D representation could be limited to a particular plexus, using methods described above, to limit the data displayed to a particular location in the retina. The location in the retina can be defined by adjacency to a particular location, such as the centroid or a boundary identified by segmentation, or the location may be limited to be between two such boundaries. In this way the 3D vessel model of each plexus could be independently reviewed.

In a further embodiment of the present invention, the examiner could select a vessel within a volume using a data input device such as a mouse or touch screen interface and the program would then highlight the connecting vessels down to the capillary level. Such visualization may improve the identification of blockages or leakages. Visualizing connected vasculature could be done, e.g. by only displaying the specific connected vasculature or by only highlighting it within the volume in order to contrast it from the other vasculature. Visualization of connected vasculature could also involve an image series or a movie, where the movie starts with only the initially selected vessel, which then grows until all the connected vessels are shown. The speed at which connecting vessels are added could be normalized by their vessel diameter in order to mimic the propagation speed of the blood within the network.

The information created by the vessel segmentation algorithms may serve as additional quantitative parameters, which could be used for comparing data sets with a normative data base or for tracking changes in a particular patient over time. Such parameters may be total vessel length, number of bifurcations, capillary density of arteriole vs. venous capillaries, vessel diameter parent/daughter vessels, bifurcation angles, vascular tortuosity, capillary network volume vs. static tissue volume.

Figure 6:
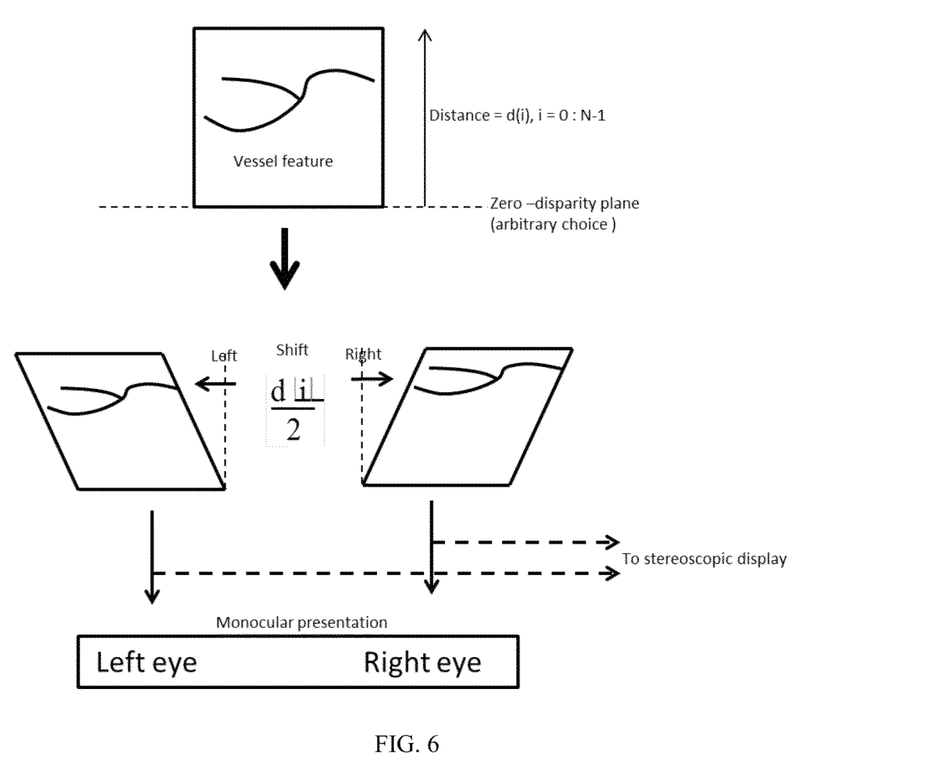
FIG. 6 illustrates how a stereoscopic image pair could be generated from motion contrast data to enable a type of 3D visualization.

In an alternative embodiment of the present invention, the actual depths of the vascular locations in the retina can be used as disparity maps to generate a stereoscopic image pair of the vascular network that can be viewed by the clinician to get a better idea of the vascular distribution in space. With the knowledge of the actual physical depth of the vascular features in the retina, a preferred scale is selected to map the range of possible distances (for example, from 0 to 2 mm), after which a left and right volume pair can be generated and fused into a stereoscopic pair as illustrated in FIG. 6. This can be rendered either through a special pair of 3D glasses, or via a 3D display technology. Extensions to this alternative embodiment also allows for augmenting this stereoscopic view by the retinal anatomy, depth encoded in the magnitude image to generate vascular maps in relation to the various layers of the retina. The vessels derived from the three plexus can be color coded preferentially to generate a more informative image fusion approach to visualization.

Figure 7:
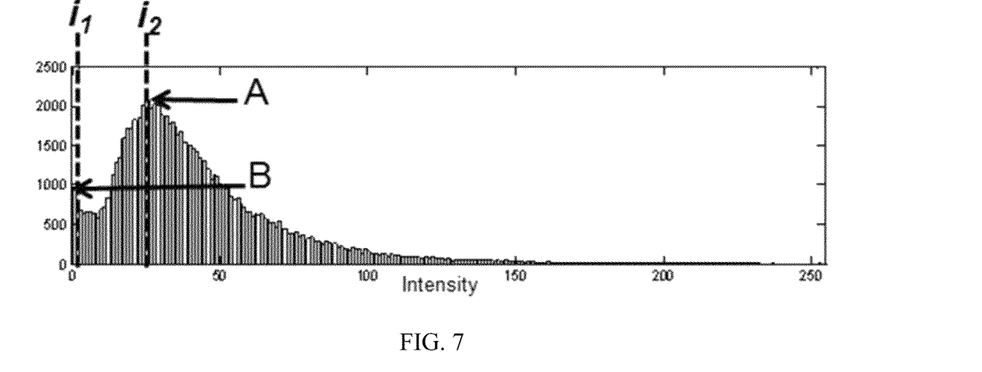
FIG. 7 shows an intensity histogram of an en face vasculature image that can be used to identify the foveal avascular zone (FAZ).
Figure 8:
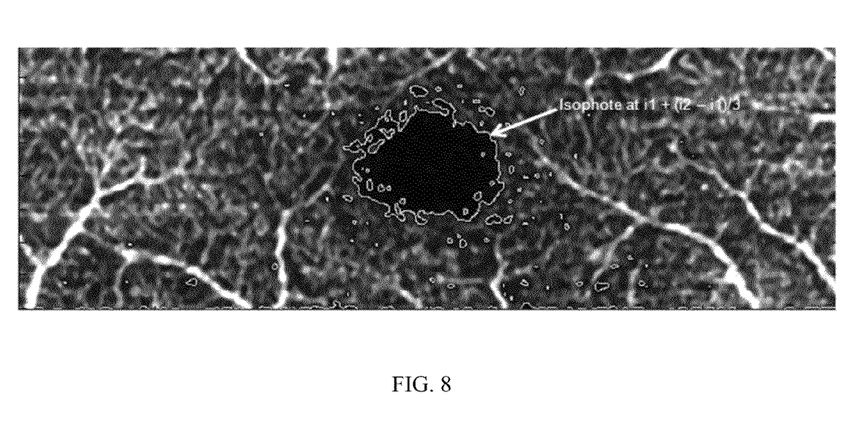
FIG. 8 shows the results of an isophote delineation of an en face vasculature image according to one aspect of the present invention.

The preferred embodiment employs the use of vasculature en face image to derive clinically significant information, the most important of which is the automated detection of the foveal avascular zone, or FAZ. The detection of the FAZ used the output of process A (FIG. 1), and can be accomplished by creating an intensity histogram of the vasculature en face image. The intensity histogram (FIG. 7) is a very popular graphing technique in image processing to generate a frequency distribution (represented along the ordinate of the graph) of the intensity values in the image which are represented along the abscissa. Many software systems contain standard and optimized libraries for the generation of the image histogram. The preferred embodiment starts the detection process by detecting the peaks of the histogram. As illustrated in FIG. 7, histogram of the vascular en face image shows a characteristic bi-modal distribution, and, the transition between the FAZ and the rest of the map is located between these peaks A and B. This is an empirical observation, and holds true for a large set of vascular enface image. The preferred embodiment estimates this transition zone as intensity level $i=i1+(i2-i1)/3$. After calculating this characteristic intensity value, the en-face image is interrogated for pixels which have this specific intensity value. Lines of similar intensity are called isophotes, and the trace of the isophote at intensity level i provides the preferred embodiment with a discriminating contour which maximally contains the FAZ on the inside, and the vascular retina on the outside (FIG. 8). The isophotes are generally delineated by a contour operation which entails thresholding the intensity levels on the image with a small neighborhood of the required isophote at level I as indicated by the arrow in FIG. 8.

The results of the isophote delineation are shown in FIG. 8. Because of the noisy nature of the signal, some small isolated contours can also be seen, but the algorithm employed in the preferred embodiment ensures that the isophote that is convex and has the largest perimeter will always enclose the FAZ. During the contour generation process to select the desired isophote, the preferred embodiment reports multiple matches (small isolated contours in FIG. 8) as a list of a list of x- and y-coordinates of each contour. These coordinates can be used in a straightforward way to calculate the perimeter of each contour. The contour that best delineates the FAZ is the one with the highest perimeter.

Figure 9:
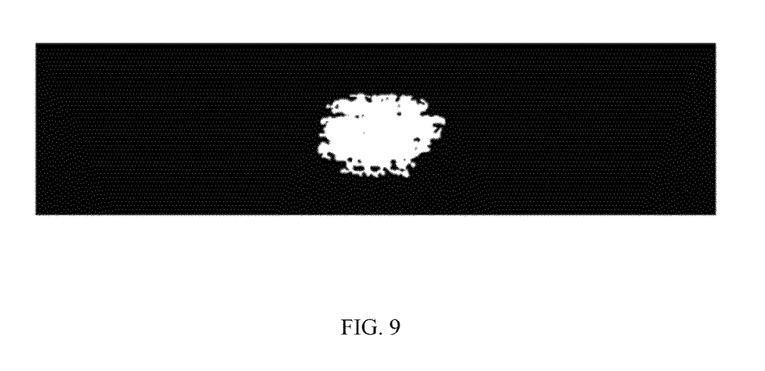
FIG. 9 illustrates how the FAZ can be isolated from the rest of the image data after the isophote delineation in FIG. 8.
Figure 10:
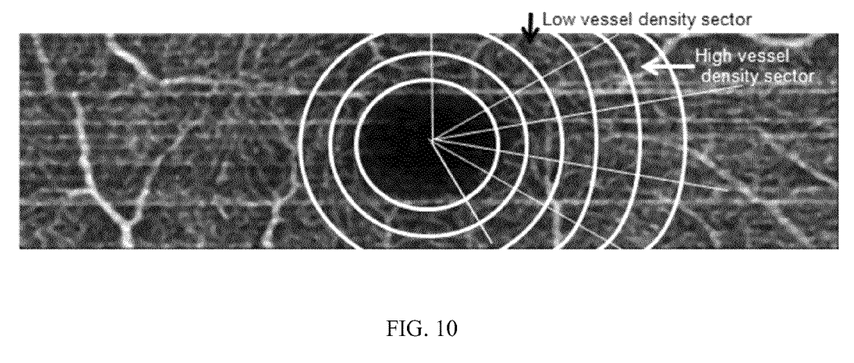
FIG. 10 shows a map of the density of vessels in radially distributed sectors around the fovea.

The region inside the FAZ contour can be isolated from the rest of the contours as illustrated in FIG. 9. Once the isophote distribution has been isolated as described in the previous paragraph, and cleaned by basic morphological operations like erosion and dilation, or any combination thereof, morphological parameters of the resulting FAZ region can be calculated to quantify the FAZ on a case by case basis. As an example of a possible quantification, for the case of FIG. 9, the area is calculated as counting the number of "on" pixels, scaled by the area of each pixel, and is 5675 pixel units. In this case the delineated FAZ has an eccentricity of 0.71 with a major axis of 104.7 pixel units (523.5 microns) and a minor axis of 73.1 pixel units (548.5 microns). In an alternative embodiment, the remainder of the vascular map (exterior to the delineated FAZ) can be used to calculate capillary density, especially as a function of distance from the center of the fovea, and generate a map of the density in radially distributed sectors around the fovea as illustrated in FIG. 10. With the knowledge of the position of FAZ in the vascular en-face, radial sectors can be analyzed and the ratio of "on" to "off" pixels can be used to generate a coarse sectorial vessel density map. The definition of the "on" and "off" pixels can be established by a judicious threshold selection.

For cases for which there is a significant encroachment of capillary network in the FAZ, an alternative embodiment (process C, FIG. 1) allows the use of prior knowledge of the fovea from the magnitude image using a fovea detection algorithm (see for example U.S. Pat. No. 8,079,711 hereby incorporated by reference) to create a localized histogram and hence confine the search for the vascular-avascular transition zone to a smaller area. In such cases, the FAZ detection by the preferred embodiment on images generated by process A will most likely fail to qualify the maximum perimeter criteria. Such a case will be flagged by a null (zero) FAZ detection (i.e., a blank image in FIG. 9) after morphological cleaning steps. Using the prior knowledge of the location of the fovea using the fovea detection algorithm will help boot-strap the detection process very close to the expected location of the FAZ. Those skilled in the art may realize that it is possible to modify the control flow to take alternative routes to detecting the FAZ in case the vascular pathology is severe at the fovea.

Other clinically significant quantifiable characteristics or metrics that can be derived from the en face vasculature image (from one or more plexus) or from a 3D OCT angiography data volume include total capillary volume (sum of all pixels above a given threshold intensity), as well as metrics that could be derived from the blood vessel patterns, such as tortuosity, regularity, segment length, total crossings, the number of bifurcations, vessel width parameters, ratio of small to large vessels, capillary density, capillary density ratio between arteriole and venous capillaries, capillary diameter, inter-capillary distance, area bounded by capillary loops, etc. It is also possible to consider including relationships between metrics derived in different plexuses, such as ratios or differences, or relationships between metrics derived in different regions of the eye, such as in the peri-fovea and extra-fovea, the fovea, the papillomacular bundle, and the optic nerve head area. Once a metric is determined, it can be compared to a database of normal eyes or eyes with a known pathology to diagnose or to track progression of a particular disease or condition.

Another way to use this information is to use the foveal avascular zone as a region over which to evaluate other features such as layer thickness or other parameters derived from the OCT image, or other registered images. For instance, the thickness of the photoreceptor layer within the FAZ should be specifically related to cones rather than rods. Registration to images that contain other information about the photoreceptors, such as adaptive optics images, might allow quantification of multiple metrics that affect the foveal region. Presentation of the vessel image compared to a simultaneously acquired image using a different modality (such as fundus imaging) would assist in using the vessel data to guide review of other modalities and vice versa. Such a common display is described in US Patent Publication No. 2008/0100612 hereby incorporated by reference.

Visual comparison of the capillary network on different visits (in one or more plexus) might reveal changes associated with progressive diseases such as diabetic retinopathy. Longitudinal analysis of any of the metrics discussed above, especially the area of the FAZ could also reveal progressive damage. The longitudinal analysis could also measure modifications in the retinal vasculature such as changes in areas of non-perfusion due to ischemia or development of DR related conditions such as IRMA. After selection of a vessel in one image, the extent of the connecting vessels down to the capillary network could potentially be evaluated serially, in the initial image and in subsequently acquired and registered datasets to determine if the extent of the vessel network for that particular vessel is expanding with treatment or contracting with worsening pathology.

The preferred embodiment described above refers to visualization of retinal capillary vessels and metrics associated with these. Similar methods could be applied to the choroidal vasculature, including the choriocapillaris, Sattler's layer and Haller's layer. Although various applications and embodiments that incorporate the teachings of the present invention have been shown and described in detail herein, those skilled in the art can readily devise other varied embodiments that still incorporate these teachings. Although the description of the present invention is discussed herein with respect to the sample being a human eye, the applications of this invention are not limited to eye and can be applied to any application using OCT.

The following references are hereby incorporated by reference:

Patent References

U.S. Pat. No. 6,549,801 Chen et al. "Phase-resolved optical coherence tomography and optical Doppler tomography for imaging fluid flow in tissue with fast scanning speed and high velocity sensitivity"
U.S. Pat. No. 7,301,644 Knighton et al. "Enhanced optical coherence tomography for anatomical mapping"
U.S. Pat. No. 7,359,062 Chen et al. "High speed spectral domain functional optical coherence tomography and optical Doppler tomography for in vivo blood flow dynamics and tissue structure"
U.S. Pat. No. 8,079,711 Stetson et al. "Method for finding the lateral position of the fovea in an SD-OCT image volume"
US Publication No. 2008/0025570 Fingler et al. "Dynamic motion contrast and transverse flow estimation using OCT,"
US Patent Publication No. 2008/0100612 Dastmalchi et al. "User interface for efficiently displaying relevant OCT imaging data"

US Patent Publication No. 2011/0034803 Stetson et al. "Nonlinear projections of 3-D medical imaging data"

US Publication No. 2010/0027857 Wang "In vivo structural and flow imaging"

US Patent Publication No. 2012/0249956 Iyer et al. "Systems and methods for efficiently obtaining measurements of the human eye using tracking"

US Patent Publication No. 2012/0277579 Sharma et al. "Inter-frame complex OCT data analysis techniques"

WO 2010/129494 Wang et al "Method and apparatus for quantitative imaging of blood perfusion in living tissue"

WO 2011/097631 Wang "Method and apparatus for ultrahigh sensitive optical microangiography"

Non-Patent Literature

Al-Diri et al. "Automated analysis of retinal vascular network connectivity," Computerized Medical Imaging and Graphics, 34, 462-470 (2010).

An et al. "Optical microangiography provides correlation between microstructure and microvasculature of optic nerve head in human subjects," J. Biomed. Opt. 17, 116018 (2012).

Avakian, et al., "Fractal analysis of region-based vascular change in the normal and non-proliferative diabetic retina," Curr. Eye Res. 24, 274-280 (2002).

Fingler et al. "Mobility and transverse flow visualization using phase variance contrast with spectral domain optical coherence tomography" Optics Express. Vol. 15, No. 20. pp 12637-12653 (2007).

Fingler et al. "Volumetric microvascular imaging of human retina using optical coherence tomography with a novel motion contrast technique" Optics Express. Vol. 17, No. 24, pp 22190-22200 (2009).

Ganesan et al. "Development of an Image-Based Network Model of Retinal Vasculature," Annals of Biomedical Engineering 38(4) 1566-1585 (2010).

Jia et al., "Quantitative OCT angiography of optic nerve head blood flow," Biomed. Opt. Express 3, 3127-3137 (2012).

Kim et al. "In vivo volumetric imaging of human retinal circulation with phase variance OCT," Biomedical Optics Express, 2(6), 1504-1513 (2011).

Kim et al. "Noninvasive Imaging of the Foveal Avascular Zone with High-Speed, Phase-Variance Optical Coherence Tomography" Investigative Ophthalmology & Visual Science, 53 (1), 85-92 (2012)

Makita et al., "Optical Coherence Angiography," Optics Express, 14(17), 7821-7840 (2006).

Makita et al., "Comprehensive in vivo micro-vascular imaging of the human eye by dual-beam-scan Doppler optical coherence angiography" Optics Express 19(2) 1271-1283 (2011).

Mariampillai et al., "Optimized speckle variance OCT imaging of microvasculature," Optics Letters 35, 1257-1259 (2010).

Leitgeb, "Imaging of the parafoveal capillary network and its integrity analysis using fractal dimension," Biomed. Opt. Express 2, 1159-1168 (2011).

Leitgeb et al., "Real-time assessment of retinal blood flow with ultrafast acquisition by color Doppler FDOCT," Optics Express, 11, 3116-3121 (2003).

Leitgeb et al. "Ultrahigh resolution Fourier domain optical coherence tomography," Optics Express 12(10):2156 (2004)

Liu et al., "Intensity-based modified Doppler variance algorithm: application to phase instable and phase stable optical coherence tomography systems" Optics Express 19(12), 11429-11440 (2011).

Schmoll et al. "Imaging of the parafoveal capillary network and its integrity analysis using fractal dimension" Biomed. Opt. Express 2, 1159-1168 (2011).

Wang et al., "Frequency domain phase-resolved optical Doppler and Doppler variance tomography" Optics Communications 242 345-350 (2004).

Wang et al., "Three dimensional optical angiography," Optics Express 15, 4083-4097 (2007).

Wang et al., "Depth-resolved imaging of capillary networks in retina and choroid using ultrahigh sensitive optical microangiography," Optics Letters, 35(9), 1467-1469 (2010).

Wang et al. "Imaging Retinal Capillaries Using Ultrahigh-Resolution Optical Coherence Tomography and Adaptive Optics" Invest. Ophthalmol. Vis. Sci. 52. 6292-6299 2011

White et al., "In vivo dynamic human retinal blood flow imaging using ultra-high-speed spectral domain optical Doppler tomography," Optics Express, 11(25), 3490-3497 (2003).

Yazdanfar "Imaging and velocimetry of the human retinal circulation with color Doppler OCT," Optics Letters 25, 1448-1450 (2000).

Yong et al. "Novel Noninvasive Detection of the Fovea Avascular Zone Using Confocal Red-Free Imaging in Diabetic Retinopathy and Retinal Vein Occlusion" Retina. 52: 2649-2655 2011

Zhao et al., "Doppler standard deviation imaging for clinical monitoring of in vivo human skin blood flow," Optics Letters 25, 1358-1360 (2000).

Zheng et al. "Automated segmentation of foveal avascular zone in fundus fluorescein angiography" Retina. 51(7): 3653-3659 2010

What is claimed is:

1. An automated method for identifying areas of interest in optical coherence tomography (OCT) image data of an eye, said method comprising:
    collecting OCT image data over a plurality of transverse locations of the eye of a patient, wherein at least some of the OCT measurements are obtained at approximately the same transverse locations separated in time by a predetermined interval;
    processing the data to determine changes in the OCT measurements obtained at approximately the same transverse locations, said changes being associated with blood flow that occurs during the predetermined interval;
    generating a two-dimensional en face vasculature image from the processed data;
    analyzing the intensity content of the en face vasculature image to identify the size and shape of a particular area;
    displaying or storing the identified area, wherein the analyzing step includes:
    generating a histogram that includes the frequency distribution of the intensity values of pixels in the image data;
    estimating an intensity value between two peaks in the histogram that corresponds to a transition zone around the particular area;
    generating isophotes within the en face image based on the estimated intensity value; and
    evaluating the isophotes to identify the size and shape of the particular area.

2. A method as recited in claim 1, wherein the identified area is the foveal avascular zone (FAZ).

3. A method as recited in claim 1, wherein the identified area is a region of retinal ischemia.

4. A method as recited in claim 1, further comprising identifying layers in the retina and using these layers as boundaries in generating the en face vasculature image.

5. A method as recited in claim 1, wherein the analysis of the en face image involves generating an intensity histogram from the en face image, identifying the intensities corresponding to peaks in the histogram, determining the transition between the identified area and the rest of the vasculature as a combination of these intensities, and locating, in the en face vasculature image, regions corresponding to these intensity values.

6. A method as recited in claim 1, further comprising dividing the en face vasculature image into sectors and using intensity to determine a proportion of a vessel in a sector in relation to the background.

7. A method as recited in claim 1, further comprising generating a three dimensional representation of the retinal vasculature.

8. A method as recited in claim 1, further comprising using an additional property of the en face vasculature image in addition to intensity to identify the particular area.

9. A method for visualizing optical coherence tomography (OCT) image data of the eye, said method comprising:

collecting OCT image data over a plurality of transverse locations of the eye of a patient wherein at least some of the OCT measurements are obtained at approximately the same transverse locations separated in time by a predetermined interval;

processing the data to determine changes in the OCT measurements obtained at approximately the same transverse locations, said changes being associated with blood flow during the predetermined interval;

generating a 3D visualization of the of the processed data including blood vessels;

receiving input from an operater selecting a particular blood vessel from said 3D visualization and then highlighting the operator selected blood vessel and only those other blood vessels that are directly connected to the selected vessel down to the capillary level and that are within the collected OCT image data.

10. A method as recited in claim 9, wherein the 3D visualization is in the form of a movie and wherein connecting vessels are highlighted propagating from the operator selected vessel down to the capillary level.

11. A method as recited in claim 10, wherein the speed of highlighting propagation is determined by the vessel diameter.

12. A method as recited in claim 1, wherein the identified area is a region of the retina that is devoid of capillaries.

13. A method as recited in claim 1, wherein the identified area is a region of non-perfusion.

* * * * *